United States Patent [19]

Hoffman

[11] 4,359,454

[45] Nov. 16, 1982

[54] METHOD AND COMPOSITION CONTAINING MCA FOR FEMALE STERILIZATION

[75] Inventor: Allan S. Hoffman, Seattle, Wash.

[73] Assignee: World Health Organization, Geneva, Switzerland

[21] Appl. No.: 217,149

[22] Filed: Dec. 16, 1980

[51] Int. Cl.³ .............................................. A61K 49/04
[52] U.S. Cl. ............................................. 424/5; 424/81
[58] Field of Search ....................................... 424/5, 81

[56] References Cited

U.S. PATENT DOCUMENTS 3,360,124  12/1967  Stonehill ............................. 206/84
3,896,077   7/1975  Leonard et al. ................. 260/42.48
4,086,266   4/1978  Corey ............................. 260/465.4

OTHER PUBLICATIONS

Freeney et al., Diagnostic Radiology, 7/79, pp. 51-60.
Neuwirth et al., Contraception, 12/77, vol. 16, No. 6, pp. 581-589.
Physicians Desk Reference (Radiology), pp. 75-85, 1978-1979.
Neuwirth et al., Am. J. Obstet. Gynecol., vol. 136, No. 7, pp. 951-956, 4/80.
Cromwell et al., AJR: 132, 5/79, pp. 799-801.
Neuwirth et al., Am. J. Obstet. Gynecol., vol. 129, No. 3, pp. 348-349, 10/77.
Stevenson et al.-Journal of Obstetrics & Gynaecology of British Comm., 11/72, vol. 79, pp. 1028-1039.
Chemical Abstracts 76:117530h, (1972).

*Primary Examiner*—Leonard Schenkman
*Attorney, Agent, or Firm*—Cushman, Darby & Cushman

[57] ABSTRACT

A method of female sterilization which comprises instilling methyl cyanoacrylate and radiopaque additive in the oviduct, allowing the methyl cyanoacrylate (MCA) to polymerize and induce an inflammatory response on the inside lining of the oviduct such that dense fibrous scar tissue is deposited across the oviduct lumen and the oviduct is occluded by natural scar tissue. The radiopaque additive permits the instillation to be examined by X-ray to insure proper positioning of the formulation and resultant blockage of the oviduct. The polymerized methyl cyanoacrylate degrades and is readily cleared along with other components of the formulation from the oviduct. In one embodiment the MCA and radiopaque additive are instilled together in liquid water-free form although they may also be instilled separately. The latter embodiment permits the use of aqueous systems for the radiopaque material. Acid and free radical polymerization inhibitors should also be used to prevent premature polymerization. Isobutyl cyanoacrylate may also be used with the MCA.

7 Claims, No Drawings

METHOD AND COMPOSITION CONTAINING MCA FOR FEMALE STERILIZATION

BACKGROUND AND SUMMARY OF THE INVENTION

The present invention is concerned with a method for inducing female sterilization and to compositions for use in such method.

Broadly stated, the method of the invention involves blocking the fallopian tubes or oviducts by using radiopaque additives in conjunction with a composition which causes inflammation of the inside or mucous lining of the tubes so as to generate scar tissue sufficient to block the tubes. The composition itself is biodegradable and leaves no residue, the oviducts being closed solely by the scar tissue which is subsequently formed. The ratiopaque additive should also be rapidly cleared from the oviducts and the body.

The invention contemplates using methyl cyanoacrylate (MCA) as the composition for effecting the desired inflammation and formation of scar tissue in the tubes. Cyanoacrylates are known to be adhesives and certain cyanoacrylates, e.g. isobutyl cyanoacrylate (IBCA) have been used for therapeutic embolization to obliterate blood vessels. See, for example, "Modification of Cyanoacrylate for Therapeutic Embolization: Preliminary Experience" by Cromwell et al, AJR: 132, May 1979, pages 799–801. Cromwell et al indicate that the cyanoacrylates suffer from two main disadvantages when used as tissue adhesives i.e they polymerize so rapidly on contact with ionic materials, e.g. blood, that a physician only has 1–2 seconds to make the needed injection; and they are not radiopaque. Cromwell et al have shown that the IBCA polymerization or set-up rate can be slowed and also that the formulation can be made suitably radiopaque for therapeutic embolism by adding iophendylate, i.e ethyl-10-(iodophenyl) undecanoate, to the cyanoacrylate.

Freeny et al in a paper entitled "Long-Term Radiographic-Pathologic Follow-Up of Patients Treated With Visceral Transcatheter Occlusion Using Isobutyl-2-Cyanoacrylate (Bucrylate)", Diagnostic Radiology, July 1979, pages 51–60, have described additional work regarding the use of IBCA for therapeutic thrombotic occulsion.

The purpose of the work referred to in the Cromwell et al and Freeny et al papers noted above is fundamentally different from that of the present invention. More specifically, the purpose of using IBCA according to the aforementioned papers is to occlude blood vessels, while causing as little as possible inflammatory response of the blood vessel wall and surrounding tissues and organs. This is called "transcatheter occlusive therapy", the blood vessels being occluded with blood clot (thrombus) plus polymerized IBCA, which does not degrade significantly in the body. This sort of therapy can be used to occlude hemorrhaging blood vessels, to identify the extent of tumor growth, to block blood flow to tumors and to treat various blood vessel malformations. In all of these cases, the occlusion agent is polymerized IBCA which remains in place and does not degrade away.

In contrast, the MCA of the present invention functions by inducing a significant inflammatory response on the inside lining of the oviducts, such that dense fibrous scar tissue is deposited across the oviduct lumen. At the same time, the MCA polymerizes to form a polymer which degrades and disappears from the site. Thus, the oviduct becomes occluded by natural scar tissue formed as a result of the inflammation caused by the MCA with no residues of the resultant MCA polymer remaining. It will thus be seen that the MCA in the present case functions in a completely different way from the IBCA used for transcatheter occlusive therapy according to Cromwell et al and Freeny et al.

The possibility of using MCA to block the fallopian tubes for sterilization purposes has previously been described. See, for example, paper entitled "The Effect of Methyl Cyanoacrylate Tissue Adhesive on the Human Fallopian Tube and Endometrium" by Stevenson et al, The Journal of Obstetrics and Gynaecology of the British Commonwealth, Nov. 1972, Vol. 79, pp. 1028–1039. This use of MCA is also disclosed by: Neuwirth et al, Am. J. Obstet. Gynecol., Vol. 129, No. 3, pp. 348–349, Oct. 1, 1977; Neuwirth et al, Contraception, December 1977, Vol. 16, No. 6, pp. 581–589; Corfman et al, Science, Vol. 148, pp. 1348–1350, June 1965; and Neuwirth et al, Am. J. Obstet. Gynecol., Vol. 136, No. 7, pp. 951–956, Apr. 1, 1980.

While the abovementioned publications disclose the use of MCA for female sterilization, they do not disclose the unique combination of the present invention, i.e. the use of MCA together with a low viscosity, water-immiscible radiopaque compound which is miscible with the MCA and which may also serve to lengthen the shelf-life of the MCA, while at the same time conferring the essential X-radiopacity to the mixture. Advantageously the selected radiopaque additive is one which tends to retard the cyanoacrylate set-up time, e.g. the material known as "Pantopaque". This can be an advantage in avoiding premature set-up in the uterus and blockage of the UTJ (uteral-tubal junction) which would prevent entry of the mixture into the tubes. Furthermore, once the composition enters the oviducts, the slower set-up rate can permit better filling of the tubes, both in cross-section and lengthwise. The radiopaque additive used according to the invention may or may not incite an acute inflammatory response (i.e., it may or may not be a sclerosing agent, as is the MCA). However it should be cleared from the body reasonably quickly and to an extent such that there are no undesirable long-term effects. The radiopaque nature of the additive is desirable to aid in visualizing whether or not the tubal blockage is bilateral and otherwise adequate. It may also be useful in training paramedical personnel and has the potential for raising the success rate for bilateral occlusion on one visit.

A preferred radiopaque additive is ethyl-10-(iodophenyl) undecanoate which is commercially available as the aforementioned "Pantopaque" (Lafayette Pharmacal, Inc.). This compound has the formula:

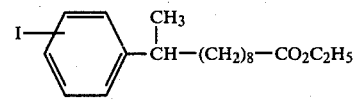

Other iodinated organic compounds may also be used as the ratiopaque additive e.g. ethiodized ethyl esters of the fatty acids of poppyseed oil (available as "Ethiodol" from Savage Laboratories) or aqueous organic iodides reacted to make them water-immiscible. Variations of these compounds are also possible such as more highly iodinated analogues of "Pantopaque" or the ethiodation esters of the fatty acids of vegetable or flower oils, fish oils, etc. Essentially any water-immiscible organic compound containing aromatic rings or unsaturated groups may be halogenated (e.g., iodinated, brominated, etc.) to yield a cyanoacrylate-miscible, radiopaque stabilizing additive suitable for use herein.

It is also possible to use radiopaque additives other than organic halides. Examples of such additives include: tantalum powder, silica powder, barium sulfate powder, Teflon powder, polyvinyl chloride (PVC) powder, calcium carbonate powder, silver powder, silver compounds and bismuth compounds. In this connection, attention is called to U.S. Pat. No. 3,896,077 which describes adhesive paste compositions comprising alpha-cyanoacrylic acid esters, including MCA, and certain insoluble inorganic fillers, e.g. calcium carbonate. Some of the MCA-paste compositions described in U.S. Pat. No. 3,896,077 may be used for present purposes although it is preferred to use "Pantopaque" or equivalent additive.

As a further modification the radiopaque substance may be attached to the cyanoacrylate itself, e.g. as iodomethylcyanoacrylate of the formula:

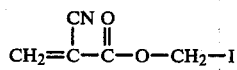

or as iodophenylcyanoacrylate of the formula:

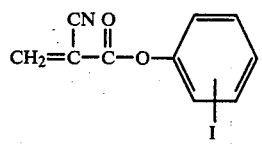

In certain situations this sort of modification may have the advantage of enhanced polymerization rate and set-up time for the liquid mixture when compared with mixtures of, for example, MCA and Pantopaque.

It will be appreciated from the foregoing that the present invention contemplates the use of a liquid mixture for tubal instillation which will induce female sterilization by bilateral blockage of both oviducts, resulting from natural fibrous tissue deposition within the tubes. The liquid mixture is further characterized by the following properties: it sets up or solidifies rapidly although in a desirably controlled fashion, by polymerization, so to avoid spillage into the peritoneum; it is radiopaque in order to verify bilateral entrance; it induces a significant local inflammatory ("toxic") response within the tubes; it disappears by biodegradation and diffusion of breakdown products and radiopaque additives as fibrous tissue is deposited in its place; and it does not cause any other undesirable response within the body.

In some cases the radiopaque additive may tend to undesirably slow the setting of the instillation mixture. In that event it may be desirable to include in the mixture another additive which is intended to speed up the rate of solidification or polymerization of the liquid mixture in vivo, i.e. after it is instilled into the oviducts, in order to avoid spillage into the peritoneal cavity. For this purpose, a faster-curing cyanoacrylate (e.g. IBCA) may be mixed with the MCA and radiopaque additive to provide a liquid water-free mixture for use according to the invention. However, since MCA is the most active of the alkyl cyanoacrylates in eliciting an inflammatory response and subsequent fibrous tissue deposition, and since poly-MCA is the only poly-cyanoacrylate which biodegrades at a significant rate, any modification of the mixture to include IBCA or other additives needs to be clearfully designed (e.g. to avoid segments of pure poly IBCA in the cured polymer). Thus, it is anticipated that at most up to ca 20% (vol.), and preferably not more than 10%, of IBCA may be mixed with MCA to achieve the optimum behavior of rapid curing and reasonably rapid polycyanoacrylate biodegradation and disappearance accompanied by scar tissue deposition.

Other essential additives to the cyanacrylate and radiopaque substance formulation include polymerization inhibitors to enhance the shelf life of the formulation and to inhibit premature curing before the system sets up in the oviduct. Two types of such inhibitors should be used: (1) acids such as $SO_2$, p-toluene sulfonic acid, formic acid, acetic acid, etc. and (2) free radical traps such as hydroquinone, hindered phenols and their derivatives. The acid inhibitors will usually be used in the amount of from 0 to 5% by volume (based on the MCA), preferably from 0.01 to 3%. The amount of free radical stabilizers will usually be in the range of 0 to 5% by weight of MCA, preferably 0.01 to 1% by weight.

Ideally, the components making up the liquid water-free mixture of the invention are totally miscible with each other to give a single phase composition. The presence of multiphases may cause instillation problems, e.g. plugging of the injector used to insert the mixture. Multiphase compositions can be used but extra precaution must be taken to avoid such plugging.

As a further modification of the invention it is also contemplated that two separate solutions may be sequentially or simultaneously but separately instilled rather than using a single mixture. For example, an aqueous radiopaque solution and liquid MCA may be injected separately but more or less simultaneously to the desired body site. One possible sequence is as follows: (a) instill the aqueous or organic radiopaque additive system, (b) take an X-ray, (c) instill the MCA, and (d) take another X-ray to verify tubal blockages by the movement of the radiopaque fluid in the oviducts. This could be important in permitting use of aqueous radiopaque additives (which would normally cure the MCA if mixed with it) in a sequence with the non-aqueous MCA instillation.

As an illustration of a composition suitable for present purposes there may be mentioned a blend of 25% by volume of Pantopaque dissolved in MCA. Such a mixture was prepared by blending the Pantopaque in the MCA in the absence of moisture. The mixture (MCA/P) was stored in the dark at room temperature (20°-25° C.). It retained its original low viscosity, free-flowing liquid condition even after storage for 10 months. Samples of MCA/P (25%) mixtures were also instilled into sections of freshly excised human oviducts. X-rays showed the tubes were filled with the MCA-Pantopaque mixture.

The amount of radiopaque additive used according to the invention can be varied depending on the nature of the additive itself and other factors. With Pantopaque as the additive, optimum results appear to be obtained with a mixture as described above comprising about 25% by volume of additive, based on the total volume of additive and MCA. However, it will be appreciated that the amount of Pantapaque and/or other additive can be varied over a relatively wide range to give the desired degree of radiopaqueness and set-up time.

The invention is illustrated by the following examples involving the instillation of mixtures of MCA and Pantopaque into cellophane, glass and freshly excised rabbit and human oviducts:

EXAMPLE 1

X-ray of Pantopaque/MCA (P/MCA) mixtures injected into cellophane tubing

Mixtures of P and MCA in ratios of 0, 0.1, 0.2, and 0.3 P/MCA were injected into 3 mm diameter cellulose tubing at 15 psig, in saline solution at pH=7.5. The tubes were removed from the bath, dried and X-rayed. All tubes were visible in the X-ray except the 0% P. Similar X-rays using a plastic pelvic phantom showed that only the 20 and 30% P specimens could be clearly seen.

EXAMPLE 2

Effect of Pantopaque on flow and setting of MCA mixtures in cellophane tubes

Mixtures with a total volume of 0.5 ml were made of MCA with increasing amounts of Pantopaque up to a volume fraction of 0.5 for Pantopaque (that is, 50% by vol of Pantopaque, 50% by vol. of MCA). Each was injected at 26 psig pressure into 2.5 mm diameter cellophane tubes immersed in and previously wetted internally by Hank's solution at pH 7.5, 37° C. The distance penetrated by the mixture along the cellophane tube first rose and then fell as the Pantopaque increased to a volume fraction of 0.5. It would appear that the Pantopaque at first retards the setting up of MCA permitting greater penetration, but at higher concentrations the high viscosity of the Pantopaque itself retards the penetration of the mixture along the tube.

EXAMPLE 3

Injections of Pantopaque-MCA mixtures into glass tubes

100% MCA and 25% Pantopaque, 75% MCA were injected at 26 psig through 18 gauge needles into rigid glass tubes, previously irrigated internally with Hank's solution at pH 7.5 and 37° C. The general appearance of the 100% MCA and 75% MCA/25% Pantopaque mixture was similar. Evidence of similar mixing charactor was seen by the similar fractional length of foamed regions of the cured mixtures.

EXAMPLE 4

Instillation of MCA/Pantopaque mixtures into freshly excised rabbit oviduct

Two oviducts were removed from a sexually mature NZW rabbit doe. The fat pad was trimmed away and the folds at the UTJ were removed in order to expose the osteum of the oviduct. The oviducts were equilibrated in Hank's solution at pH 7.5, 37° C. for one hour prior to injection. The oviducts were also flushed with about 5 cc Hank's just before instillation. Two mixtures of MCA and Pantopaque (0 and 25% P) were injected into the two oviducts and polymerized in situ. A flat tip 18G needle was used in the injector and 0.3 cc was injected at 20 psig. The flow rate was estimated to be about 1.2 m./sec for the 100% MCA and about 0.9 ml/sec for the 75% MCA/25% P. The oviducts were taken from the bath one hour post injection and the tissue was removed. Photomicrographs were taken at about 8X and linear measurements were made on the photographs of the length of the instillation. The following approximate values were obtained for the distance of the injection:

| 75% MCA/25% P | 115 ± 2 mm |
|---|---|
| 100% MCA | 97 ± 2 mm |

After removal of the tissue, the 25% P/75% MCA polymerized system appeared to be somewhat softer than pure polymerized MCA and contained somewhat more foamed regions, while also displaying a "grainier" appearance on the surface. Both mixtures replicated the inner oviductal surface wall.

EXAMPLE 5

Injection of Pantopaque-MCA mixtures into freshly-excised human oviducts

Freshly-excised human oviducts were obtained, washed in saline, and within one hour were injected manually using a syringe with 10, 15, and 25 vol% Pantopaque until the MCA/P mixture could be seen coming out the other end of the tube specimen. The filled tubes were placed in the refrigerator until the following morning, when they were X-rayed using an appropriate pelvic tissue phantom. It could be seen that the tube became clearly and unequivocally visible in the X-ray at 25% Pantopaque.

EXAMPLE 6

Sequential instillation of radiopaque systems and then MCA into freshly-excised rabbit oviducts Sequential (syringe) instillations of Pantopaque followed by different volumes of MCA were made into freshly-excised rabbit oviducts. The folds located at the UTJ were trimmed as before. The oviducts were allowed to come to equilibrium in the bath (Hank's solution) for one hour at 37° C., pH 7.5 First, 1 cc of Pantopaque were instilled into three oviducts (such that the total oviduct was filled), followed five minutes later in three different cases by 0, 0.1, or 0.2 cc of MCA. Injection was performed using 20 psig and a flat tip 18G needle with a spacer to pull the needle tip back from the urterus by about 4 mm to prevent puncture of the tissue. (This is different than the glass tube studies where the tip of the needle protruded into the glass tube about 2 mm.) Two minutes post-injection the two ends of the oviduct were ligated. The entire oviduct was then removed and stored in the refrigerator until X-rays could be taken the next day. In the X-rays, it could be clearly seen that the Pantopaque had moved further down the tube after the MCA had been instilled.

The same procedure was used with Amipaque, an aqueous-base radiopaque system. In the Amipaque study, the Amipaque was mixed with 4.2 ml of sodium bicarbonate to make a 280 ml 1/ml solution. This solution was the one recommended by the suppliers for hysterosalpingograms. An X-ray was taken. 0.2 cc MCA was then instilled at 20 psig, 36.8° C., pH 7.5. The X-rays after the first and second instillations revealed that the Amipaque had been "spread out" in the tube by the instillation of MCA. The intense radiopacity had become broken up by the passage and curing of MCA within the oviduct, confirming entrance into the oviduct by the MCA.

Two representative formulations which are suitable for use in practicing the invention are the following:

A

75% MCA
25% Pantopaque
200 ppm SO$_2$
500 ppm hydroquinone

B

72% MCA
25% Pantopaque
3% acetic acid
500 ppm hydroquinone.

It will be appreciated from the foregoing that various modifications may be made in practicing the invention. Broadly speaking, the compositions of the invention may be described as liquid, water-free formulations comprising MCA and a sufficient amount of the radiopaque material to determine by X-ray that the formulation has been properly positioned and that effective blockage of the oviducts has occurred. Usually the amount of radiopaque additive will fall in the range of 10–50%, preferably 20–25%, based on the formulation volume. Where IBCA or other alkyl cyanoacrylate or the like is also included, this may comprise up to 20, preferably up to 10%, based on the volume of the formulation. In the case of the two-part system where the radiopaque additive is in aqueous form and is instilled separately from the MCA, it appears that generally the same amount of additive can be used as in the case where the components are mixed together for instillation. It appears however, that, in the case where an aqueous suspension of a radiopaque solid such as tantalum is used, the preferred amount would normally fall in the range of 1–10% by weight based on the weight of the MCA.

Other possible variations will also be evident from the foregoing and the following claims wherein:

What is claimed is:

1. In a method of female sterilization which comprises instilling liquid water-free methyl cyanoacrylate in the oviduct whereby the methyl cyanoacrylate polymerizes and degrades to induce an inflammatory response on the lining of the oviduct such that dense fibrous tissue is deposited across the oviduct lumen and the oviduct is thereby occluded by natural scar tissue, the improvement which comprises using the methyl cyanoacrylate polymer with ethyl-10-(iodophenyl) undecanoate so that the positioning of the methyl cyanoacrylate instilled in the oviduct can be determined by X-ray eximination.

2. The method of claim 1 wherein the formulation includes up to 20% by volume of another faster-curing cyanoacrylate.

3. The method of claim 2 wherein the other cyanoacrylate is isobutyl cyanoacrylate.

4. The method of claim 1 wherein the formulation includes an acid and a free radical polymerization inhibitor present in an amount sufficient to prevent premature polymerization.

5. A liquid, water-free formulation for use in female sterilization which consists essentially of methyl cyanoacrylate; 10–50% ethyl-10-(iodophenyl) undecanoate based on the volume of the formulation from 0.01 to 3% by volume of an acid polymerization inhibitor, based on the methyl cyanoacrylate content, and from 0.01 to 1% by weight of a free radical polymerization inhibitor, based on the weight of methylcyanoacrylate, the inhibitors being present in amounts sufficient to prevent premature polymerization.

6. A formulation according to claim 5 wherein the formulation weighs up to 20% by volume of another faster-curing cyanoacrylate.

7. A formulation according to claim 6 wherein the other cyanoacrylate is isobutyl cyanoacrylate.

* * * * *